US009833535B2

(12) United States Patent
Pugh et al.

(10) Patent No.: US 9,833,535 B2
(45) Date of Patent: Dec. 5, 2017

(54) CONTACT LENS STORAGE CASE SURFACE DISINFECTION

(71) Applicant: Johnson & Johnson Vision Care, Inc., Jacksonville, FL (US)

(72) Inventors: Randall B. Pugh, Jacksonville, FL (US); Edward R. Kernick, Jacksonville, FL (US); William C. Neeley, Melbourne, FL (US); Dwight Abouhalkah, Jacksonville, FL (US); Leslie A. Voss, Jacksonville, FL (US); Karson S. Putt, Jacksonville, FL (US); James D. Riall, St. Johns, FL (US)

(73) Assignee: Johnson & Johnson Vision Care Inc., Jacksonville, FL (US)

( * ) Notice: Subject to any disclaimer, the term of this patent is extended or adjusted under 35 U.S.C. 154(b) by 0 days.

(21) Appl. No.: 14/692,539

(22) Filed: Apr. 21, 2015

(65) Prior Publication Data

US 2015/0250915 A1 Sep. 10, 2015

Related U.S. Application Data

(63) Continuation of application No. 13/118,931, filed on May 31, 2011, now Pat. No. 9,024,276.

(60) Provisional application No. 61/357,786, filed on Jun. 23, 2010.

(51) Int. Cl.
| | |
|---|---|
| G01N 23/00 | (2006.01) |
| A61L 12/06 | (2006.01) |
| A45C 11/00 | (2006.01) |
| G02C 7/04 | (2006.01) |

(52) U.S. Cl.
CPC .......... A61L 12/063 (2013.01); A45C 11/005 (2013.01); G02C 7/04 (2013.01)

(58) Field of Classification Search
CPC .................................. A61L 2/0047; A61L 2/10
USPC .............. 250/453.11, 454.11, 455.11, 492.1; 210/748.1; 356/51; 359/350; 422/24
See application file for complete search history.

(56) References Cited

U.S. PATENT DOCUMENTS

| | | | |
|---|---|---|---|
| 3,852,032 A | 12/1974 | Urbach | |
| 3,978,341 A | 8/1976 | Hoell | |
| 4,063,890 A | 12/1977 | Baron | |
| 4,141,956 A * | 2/1979 | Lemchen | A61L 2/18 422/116 |

(Continued)

FOREIGN PATENT DOCUMENTS

| | | |
|---|---|---|
| CN | 1269246 A | 11/2000 |
| CN | 101401949 A | 8/2009 |

(Continued)

OTHER PUBLICATIONS

Harris, M.G., et al. "Ultraviolet disinfection of contact lenses." *Optometry and Vision Science*, Oct. 1993;70(10): 839-42. Print.

(Continued)

*Primary Examiner* — Jason McCormack

(57) ABSTRACT

The present invention provides for a disinfecting radiation base for working in conjunction with a storage case for an ophthalmic lens. The disinfecting radiation base provides disinfecting radiation for disinfecting a surface of the storage case. The disinfecting radiation base may also include a processor and digital memory for automated functions associated with the base.

34 Claims, 6 Drawing Sheets

(56) References Cited

U.S. PATENT DOCUMENTS

| | | | |
|---|---|---|---|
| 4,414,956 A * | 11/1983 | Webber | F24B 1/024 |
| | | | 126/217 |
| 4,545,479 A | 10/1985 | Figari | |
| 4,868,397 A | 9/1989 | Tittel | |
| 4,899,057 A | 2/1990 | Koji | |
| 4,956,155 A | 9/1990 | Rohrer | |
| 5,082,558 A | 1/1992 | Burris | |
| 5,086,913 A | 2/1992 | Camm | |
| 5,120,499 A | 6/1992 | Baron | |
| 5,144,144 A | 9/1992 | Borovsky | |
| 5,166,528 A | 11/1992 | Le Vay | |
| 5,387,404 A | 2/1995 | Kutner | |
| 5,439,642 A | 8/1995 | Hagmann | |
| 5,618,492 A | 4/1997 | Auten | |
| 6,030,554 A | 2/2000 | Ichihara | |
| 6,039,928 A * | 3/2000 | Roberts | A61L 2/10 |
| | | | 422/186.3 |
| 6,461,568 B1 | 10/2002 | Eckhardt | |
| 6,465,799 B1 | 10/2002 | Kimble | |
| 6,507,030 B1 | 1/2003 | Briggs | |
| 6,566,659 B1 | 5/2003 | Clark | |
| 6,576,188 B1 | 6/2003 | Rose | |
| 6,592,816 B1 | 7/2003 | Ebel | |
| 6,790,409 B1 * | 9/2004 | Nakamura | A61L 12/06 |
| | | | 422/22 |
| 7,217,936 B2 | 5/2007 | Ressler | |
| 7,722,808 B2 | 5/2010 | Matsuzawa | |
| 7,879,288 B2 | 2/2011 | Brown-Skrobot | |
| 8,021,608 B2 | 9/2011 | Brown-Skrobot et al. | |
| 8,318,089 B2 | 11/2012 | Brown-Skrobot et al. | |
| 8,528,728 B2 * | 9/2013 | Pugh | A45C 11/005 |
| | | | 206/5.1 |
| 9,024,276 B2 * | 5/2015 | Pugh | A45C 11/005 |
| | | | 250/455.11 |
| 2002/0066867 A1 * | 6/2002 | Ross, III | B65B 25/008 |
| | | | 250/461.1 |
| 2002/0122743 A1 | 9/2002 | Huang | |
| 2004/0234569 A1 | 11/2004 | Nakada | |
| 2005/0013729 A1 * | 1/2005 | Brown-Skrobot | A61L 2/10 |
| | | | 422/24 |
| 2005/0079096 A1 | 4/2005 | Brown-Skrobot et al. | |
| 2005/0173652 A1 | 8/2005 | Ressler | |
| 2006/0008400 A1 | 1/2006 | Gutman | |
| 2006/0018508 A1 | 1/2006 | Monk | |
| 2006/0151715 A1 | 7/2006 | Greene | |
| 2006/0188389 A1 | 8/2006 | Levy | |
| 2007/0104611 A1 | 5/2007 | Marmo | |
| 2007/0206377 A1 * | 9/2007 | Borup | A45C 11/005 |
| | | | 362/156 |
| 2008/0067418 A1 * | 3/2008 | Ross | A61L 2/10 |
| | | | 250/455.11 |
| 2008/0199353 A1 * | 8/2008 | Mlodzinski | A61J 1/20 |
| | | | 422/24 |
| 2008/0219899 A1 * | 9/2008 | Deshays | A61L 2/10 |
| | | | 422/186.3 |
| 2009/0012466 A1 | 1/2009 | Zhao | |
| 2009/0084734 A1 | 4/2009 | Yencho | |
| 2009/0086160 A1 | 4/2009 | Enns | |
| 2009/0123331 A1 | 5/2009 | Ross | |
| 2009/0274576 A1 * | 11/2009 | Ressler | A23L 3/26 |
| | | | 422/24 |
| 2010/0320405 A1 | 12/2010 | Gardner, III | |
| 2011/0085937 A1 | 4/2011 | Brown-Skrobot et al. | |
| 2011/0243789 A1 | 10/2011 | Roberts | |
| 2011/0293471 A1 | 12/2011 | Brown-Skrobot et al. | |
| 2016/0184472 A1 * | 6/2016 | Pugh | A61L 12/063 |
| | | | 206/205 |
| 2016/0193378 A1 * | 7/2016 | Pugh | A61L 12/063 |
| | | | 250/454.11 |

FOREIGN PATENT DOCUMENTS

| | | |
|---|---|---|
| EP | 1033138 A1 | 9/2000 |
| EP | 1038536 A2 | 9/2000 |
| EP | 1038536 A3 | 4/2001 |
| EP | 1038536 B1 | 6/2005 |
| EP | 1033138 B1 | 6/2006 |
| EP | 2067491 A1 | 10/2009 |
| FR | 2599255 A1 | 12/1987 |
| JP | 2002126050 A | 5/2002 |
| JP | 2003093481 A | 4/2003 |
| JP | A-2003-093481 | 4/2003 |
| JP | 3100828 | 5/2004 |
| JP | 3100828 U * | 5/2004 |
| JP | A-07-265394 | 10/2005 |
| JP | A-2007-151756 | 6/2007 |
| KR | 20070050328 | 5/2007 |
| RU | 57423 U1 | 10/2006 |
| RU | 69323 U1 | 10/2007 |
| TW | 202793 | 3/1993 |
| TW | 283212 | 8/1996 |
| TW | M256599 | 2/2005 |
| WO | 200038740 | 7/2000 |
| WO | WO 2005/037331 A1 | 4/2005 |

OTHER PUBLICATIONS

Admoni, M.M., et al. "Disinfection efficacy in an integrated ultraviolet light contact lens care system." *CLAO J.* Oct. 1994; 20(4): 246-8. Print.

Dolman, P.J., et al. "Contact lens disinfection by ultraviolet light." *American Journal of Ophthalmology*, Dec. 15, 1989;108(6):665-9.

"UV Kills These Bugs.", *Review of Optometry*. Dec. 15, 1999 v136 i12 p62.

"Device cleans, disinfects soft contact lenses in 15 minutes.", *Ophthalmology Times.*, Apr. 15, 2004 v29 i8 p66.

PCT International Search Report, dated Sep. 13, 2011, for PCT Int'l Appln. No. PCT/US2011/040725.

* cited by examiner

CONTACT LENS STORAGE CASE SURFACE DISINFECTION

RELATED APPLICATIONS

This application is a Continuation of U.S. patent application Ser. No. 13/118,931, filed May 31, 2011, which claims priority to Provisional U.S. Patent Application No. 61/357,786, filed on Jun. 23, 2010. The entire contents of each of these applications are hereby incorporated by reference.

FIELD OF USE

This invention describes a case for storing an ophthalmic lens and, more specifically, in some embodiments, a base for receiving a case with disinfecting functionality while storing an ophthalmic lens such as a contact lens.

BACKGROUND

Maintaining a clean environment during handling of a contact lens is generally considered essential to good ophthalmic health. One aspect of cleanliness that is often not adequately considered is a clean exterior of a contact lens case. Even if a contact lens handler conscientiously engages in hand-washing and proper use of lens solutions, the efficacy of such practices is limited if pathogens, such as bacteria and fungi may be present on the exterior of a contact lens case used to store the contact lenses.

Clean hands often come into contact with pathogens on the exterior of a contact lens case during the process of removing a top to a case to access a lens stored within the case. A result of such contact is that the previously clean hands now become contaminated with pathogens. During handling of the lens and placement of the lens onto the eye, contaminated hands may pass the pathogens on to a lens that has recently been disinfected with solution inside the storage case. The result is an increased risk of a pathogen being introduced into an area of the eye of the contact lens wearer.

Hydrogel contact lenses are very popular today. These lenses are often more comfortable to wear than contact lenses made of hard materials. Many hydrogel contact lenses may be worn for more than one day. A build-up of microbial life and bacteria on the lenses during wear of the lens generally makes it desirable to periodically remove the lenses and disinfect them.

Disinfection of contact lenses traditionally entails placing the contact lens in a container or case and subjecting the contact lens to a chemical disinfectant. However, chemical disinfectants are not always as efficacious as may be desired. From time to time, a contact lens with a bacterium, mold, fungus or other type of adverse life form is reinserted into a user's eye with the result being a diseased eye. In addition, disinfecting solutions tend to be expensive and add to the total cost of using contact lenses for vision correction or cosmetic enhancement. New methods and approaches are therefore needed to disinfect contact lenses.

SUMMARY

Accordingly, the present invention includes a base for an ophthalmic lens storage case for storing reusable contact lenses and disinfecting the lenses during the storage and also disinfecting at least a portion of the lens storage case. The base is capable of generating disinfecting radiation to a surface of the storage case in a wavelength and intensity suitable to kill unwanted pathogens such as bacteria, viruses, molds, fungi and the like on the lens case.

In addition, in some embodiments, the base provides vibrational frequency mechanically sufficient to effectively dislocate expired microbials and provide increased exposure of unexpired microbials to life extinguishing radiation.

In another aspect, in some embodiments, a disinfecting radiation base includes one or more reflective surfaces, such as a mirror, for reflecting disinfecting radiation towards an ophthalmic lens storage case mounted in the disinfecting radiation base.

DETAILED DESCRIPTION OF THE INVENTION

The present invention includes methods and apparatus for disinfecting a surface of an ophthalmic lens storage case. In addition, the present invention includes a storage case for holding an ophthalmic lens while one or both of the lenses and the surface of the lens storage case is disinfected with disinfecting radiation.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

GLOSSARY

In this description and claims directed to the presented invention, various terms may be used for which the following definitions will apply:

Disinfecting Radiation: as used herein refers to a frequency and intensity of radiation sufficient to diminish the life expectancy of a life form receiving a Disinfecting Radiation Dose.

Disinfecting Radiation Dose: as used herein refers to an amount of radiation to reduce an amount of pathogen life by at least two logs on a logarithmic scale and preferably three logs or more, wherein life includes at least bacteria, viruses, molds and fungi.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

DESCRIPTION

Figure 6:
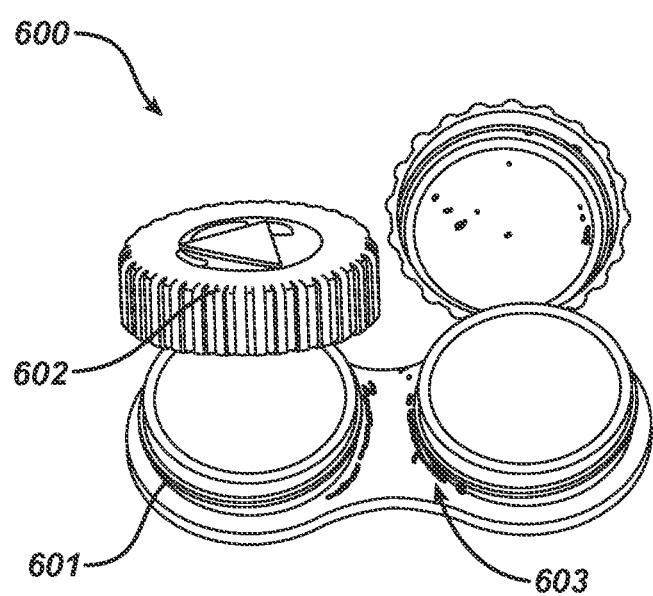
FIG. 6 illustrates a prior art contact lens storage case in a soiled condition.

Referring first to FIG. 6, an example of a contact lens storage case 600 including a storage case lens holder 601 and a storage case lid 602, is illustrated. As illustrated, in some instances a contact lens storage case 600 may accumulate significant soiling and pathogen build-up 603 on one or more surfaces of the storage case 100.

Figure 1:
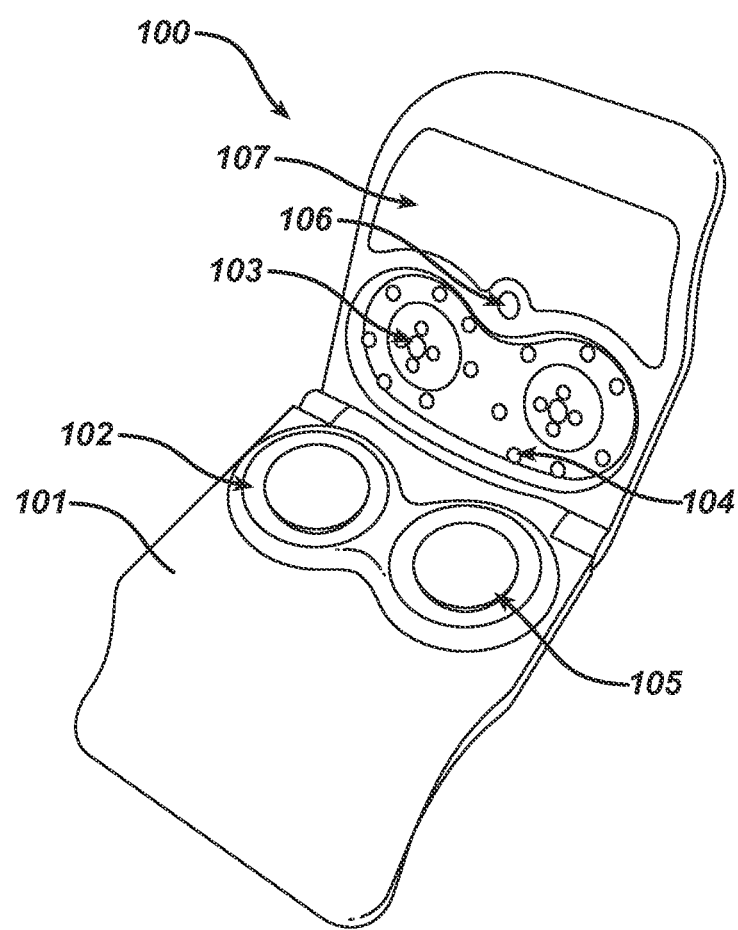
FIG. 1 illustrates a lens storage case in a base unit according to some embodiments of the present invention.

Referring now to FIG. 1, an ophthalmic lens disinfecting system 100 is illustrated including a radiation based disinfecting base 101, a radiation based disinfecting storage case 102 and one or more disinfecting radiation sources 103-104. The radiation based disinfecting storage case 102 may include a storage case lid and a storage case holder. According to the present invention, a radiation based disinfecting storage case 102 is positioned within the path of radiation from the one or more disinfecting radiation sources 103-104, such that one or both of the surface of a radiation based disinfecting lens storage case 102 and ophthalmic lenses (not illustrated) stored within the disinfecting storage case 102 are exposed to radiation emanating from the one or more disinfecting radiation sources 103-104 and pathogens existing on, or in proximity to, radiation based disinfecting lens storage case 102 are exposed to disinfecting radiation provided by a disinfecting radiation source 103-104, and killed, essentially disinfecting one or both of the ophthalmic lens and a surface of the lens storage case.

As illustrated, the ophthalmic lens disinfecting system 100 including a generally clamshell type configuration, is positioned in an open state with a radiation disinfecting base 101 and a lid 106. A radiation disinfecting storage case 102 is shown positioned in the clamshell radiation disinfecting storage system 100. In some preferred embodiments, the radiation disinfecting storage case 102 includes a positioning artifact 105 for aligning the disinfecting radiation source 103 with the radiation disinfecting storage case 102. As illustrated, the positioning artifact 105 includes an annular depression for receiving an annular arrangement of disinfecting radiation source 103. Positioning artifacts 105 may include almost any polygon shaped depression. Other embodiments may include one or more alignment pins. In still other embodiments, a positioning artifact 105 may include a snap, a threaded joining or other removably fixed type of joining.

In some embodiments, the positioning artifact 105 aligns the radiation disinfecting radiation source 103-104 in a position generally orthogonal to a top surface of a storage case 102 placed in the ophthalmic lens disinfecting system 100. In additional embodiments, a positioning artifact 105 aligns the radiation disinfecting radiation source 103 in a position generally orthogonal to a plane of a storage case 102 placed in the ophthalmic lens disinfecting system 100.

In another aspect, in some embodiments, the radiation disinfecting base 101 may also include a source of a vibrational frequency 106 capable of transmitting a vibrational frequency from a radiation disinfecting base 101 to the radiation disinfecting storage case 102 and ultimately to a lens stored within the radiation disinfecting storage case 102.

In some preferred embodiments, the vibrational frequency may be a frequency capable of causing expired life forms to be moved from within a path of radiation to an unexpired life form. Moving the expired life forms allows for more efficacious disinfecting by exposing more unexpired life forms to a direct path of radiation.

The one or more radiation disinfecting radiation source 103-104 may include one or more light emitting diodes (LEDs). In some preferred embodiments, the LEDs include ultraviolet (UV) emitting LEDs. Preferred embodiments include LEDs which emit light radiation with a wavelength of between about 250 nanometers of light radiation and about 280 nanometers of light radiation, preferably, the wavelength is between 250 nanometers and 275 nanometers, and most preferably 254 nanometers.

Figure 2:
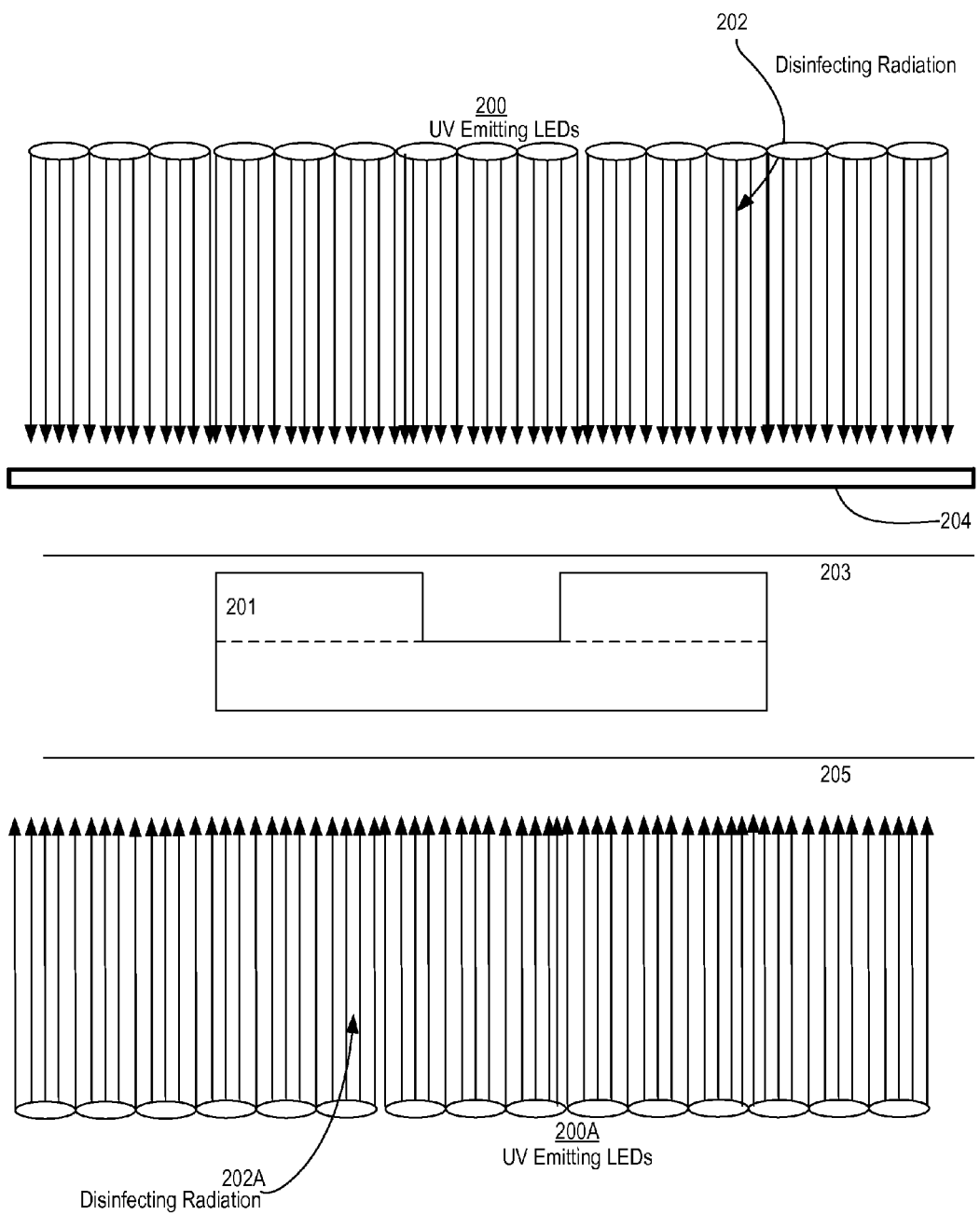
FIG. 2 illustrates some embodiments of alignment of a disinfecting radiation source with an ophthalmic lens in a lens storage case according to the present invention.

Referring now to FIG. 2, a block diagram illustrates some embodiments of alignment of a radiation disinfecting source 200, such as one or more UV LEDs radiating disinfecting radiation 202 in the UV spectrum towards a contact lens storage case 201. In some preferred embodiments, UV LEDs will be arranged such that a radiation disinfecting storage case will align in a specific position in relation to the contact lens storage case 201. The alignment is maintained via an alignment artifact.

In some embodiments, a radiation disinfecting storage case is aligned to direct UV radiation 202 at an angle essentially orthogonal to a plane 203 plane across a top portion of the contact lens storage case 201.

In other embodiments, radiation disinfecting storage case may be aligned to direct disinfecting radiation 202A from one or more UV emitting LEDs 200A at an angle essentially orthogonal to a plane 205 across a bottom of the contact lens storage case 201.

In another aspect, in some embodiments, one or more optics 204 may be used to focus disinfecting radiation onto a disinfecting radiation storage case 201. An optic may be included in a base or in a part of a storage case.

Figure 3:
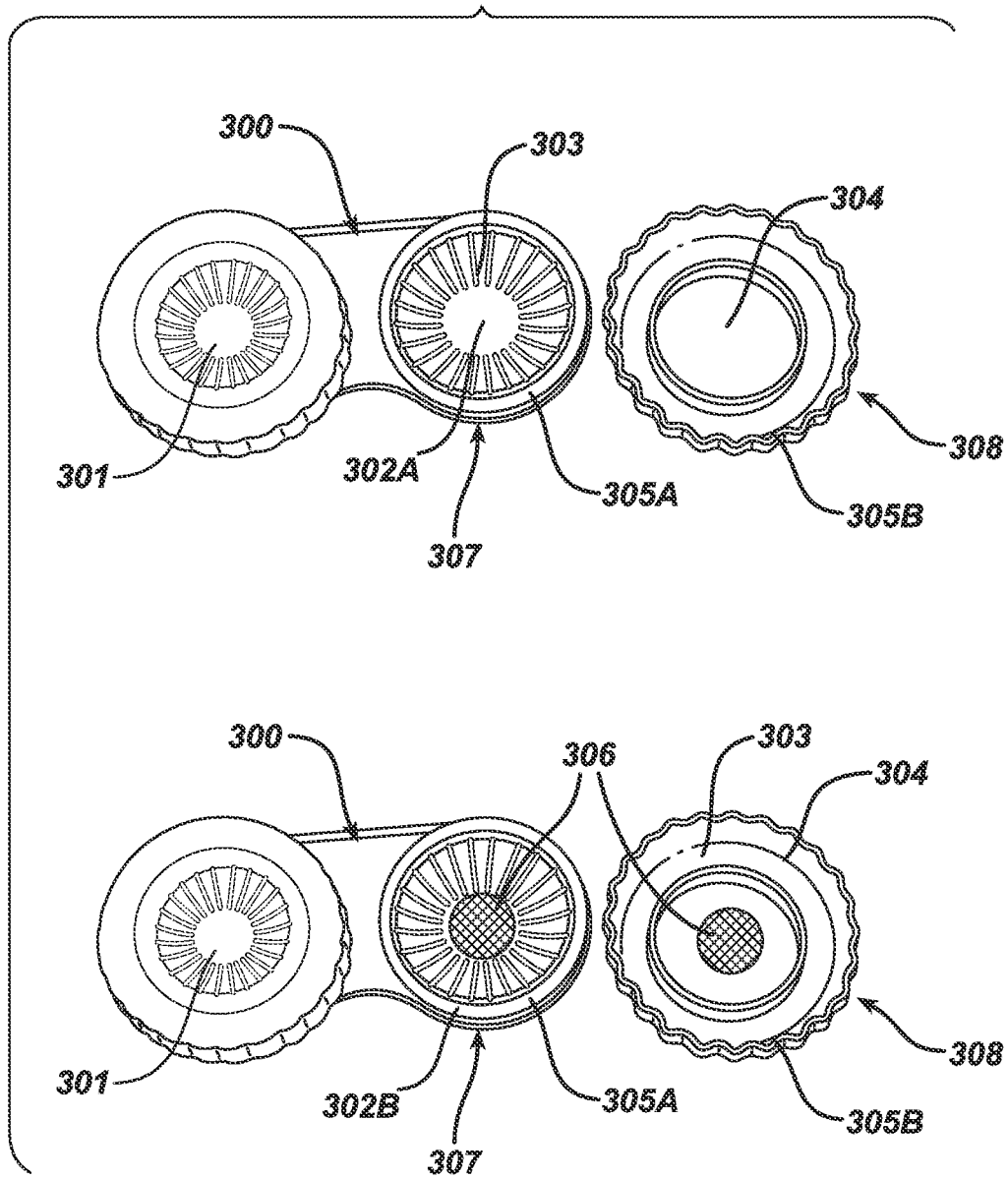
FIG. 3 illustrates a close up view of a storage case with one cap removed according to some embodiments of the present invention.

Referring now to FIG. 3, an exemplary radiation disinfecting storage case 300 is illustrated. The radiation disinfecting storage case 300 includes one or more lens storage compartments 301. A storage compartment 301 is capable of receiving and storing one or more ophthalmic lenses, such as a contact lens.

Some embodiments include one or more lens alignment mechanisms 302 for positioning an ophthalmic lens stored in a storage compartment 301 included in a radiation disinfecting storage case 300. A lens alignment mechanism 302A may include for example a pedestal with an arcuate surface generally of a similar size and shape as an inside dimension of an ophthalmic lens. A convex surface may include an arc generally equivalent to an arc of a concave surface of an ophthalmic lens to be stored within the radiation disinfecting storage case 300. Other embodiments may include a lens alignment mechanism 302B comprising a bowl generally of a similar size and shape as an outside dimension of an ophthalmic lens.

Preferred positioning aligns the stored lens in a direct path of disinfecting radiation. However, other embodiments may include one or reflective surfaces 306. A reflective surface 306 may essentially include a mirror and be formed from a glass, a plastic, a metal or a coating that is functional to reflect disinfecting radiation in a direction desired. Generally, the direction will be towards a lens stored in a storage case 300 positioned in the base. In some embodiments, reflective surface 306 may be generally proximate to, and/or generally parallel to, a surface of a stored lens. Other embodiments may include a reflective surface 306 generally around a perimeter of a stored lens.

One or more radiation windows 303-304 are included in the storage compartments 301. The radiation windows 303-304 provide portions of the radiation disinfecting storage case that are at least partially transparent to wavelengths of disinfecting radiation. Preferably the radiation windows 303-304 will be as close to 100% transparent as possible to disinfecting radiation transmitted into the storage compartment 301. Plastics that are injection moldable may be 90% or more or even 98% or more transparent to UV radiation. Specific wavelengths may include between about 254 nanometers to 280 nanometers.

In some embodiments, a radiation window may also include an optic for directing disinfecting radiation towards areas of an ophthalmic lens stored in the stored compartment 301.

Examples of materials from which the radiation windows 303-304 may be formed include, for example: cyclic olefins, TOPAS, ZEONOR or other injection moldable plastic. Other plastics or glass may also be utilized as a material for the radiation window 303-304. The area of the radiation windows 303-304 should be sufficient to admit enough disinfecting radition into the storage compartments to kill life forms present on an ophthalmic lens stored in the storage compartment 301.

Some preferred methods of manufacture of a radiation disinfecting storage case include injection molding processes. Other methods include, for example, lathing, stereo lithography, and three dimensional printing.

In another aspect, radiation disinfecting storage case 300 may include a fastening mechanism 305A-305B for securing and removing a cap 308 from a storage compartment 307. The fastening mechanism 305A-305B may include a threaded portion, a snap, and a tapered joint or other mechanism for removably securing the cap 308 to the case at the discretion of the user. While the cap 308 is secured to the storage compartment 307, the cap seals off an ambient atmosphere from the storage compartment 307 and also contains an ophthalmic lens and, in some embodiments, a solution, such as, for example a saline solution, within the compartment 307.

Figure 4:
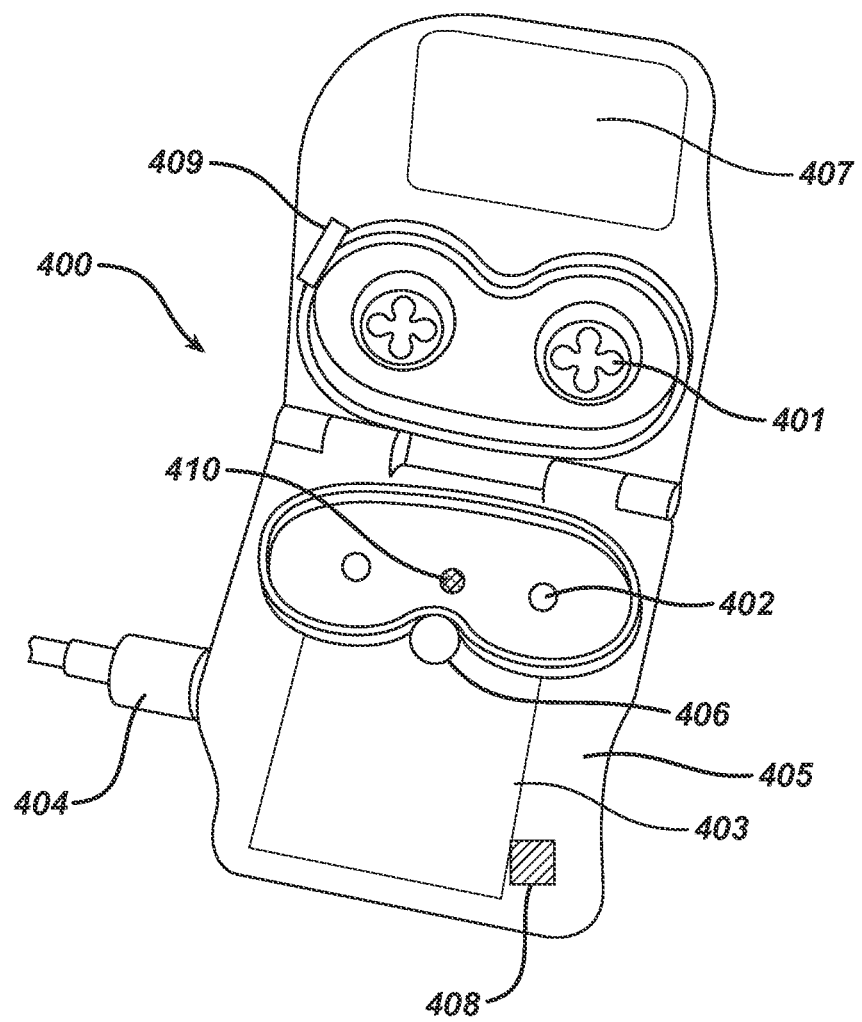
FIG. 4 illustrates aspects of a base unit according to some embodiments of the present invention.

Referring now to FIG. 4, a radiation disinfecting base unit 400 is illustrated with multiple disinfecting radiation source LEDs 401-402. As illustrated, the disinfecting radiation source LEDs 401-402 may include one or both of overhead disinfecting radiation source LEDs 401 and lower disinfecting radiation source LEDs 402. In addition to the overhead disinfecting radiation source LEDs 401 and lower disinfecting radiation source LEDs 402, the base unit may include a processor board 403 with control electronics for controlling various aspects associated with the radiation disinfecting base 400.

The processor board 403 may be coupled to a digital storage 408. The digital storage may include executable software that is executable upon command or automatically upon operation of the radiation disinfecting base unit 400. The digital storage 408 may also store data related to operation of the radiation disinfecting case 400. Operational data may include for example, time periods during which a radiation disinfecting base unit 400 is operated; serial numbers of lenses being disinfected; a period of time that a lens has been placed in use, or other information. In some embodiments, a radiation disinfecting base unit 400 may include a scanner 409 or other input means to input an identification number associated with a lens stored in a radiation disinfecting base unit 400. For example, the scanner 409 may scan a bar code or other symbol on a lens package and log disinfecting information associated with the bar code number or symbol. Information that may be logged may include for example, a number of hours that a lens has been exposed to disinfecting radiation and a number of days that a lens has been placed into use.

An electrical communication connector 404 may also be included in the radiation disinfecting base unit 400. The electrical communication connector 404 may include a universal serial bus (USB) connector or other type of connector. The connector may include a terminal for transferring one or both of data and electrical power. In some embodiments, the electrical communication connector 404 provides power to operate the radiation disinfecting base unit 400. Some embodiments may also include one or more batteries 405 or other power storage device. In some preferred embodiments, the batteries 405 include one or more lithium ion batteries or other rechargeable device. The power storage devices may receive a charging electrical current via the electrical communication connector 404. Preferably, the radiation disinfecting base unit 400 is operational via stored power in the batteries 405.

In some embodiments, the electrical communication connector 404 may include a simple source of AC or DC current.

In another aspect, the present invention may include a source of mechanical movement, such as a vibration generation device 406. The vibration generation device 406 may include, for example, a piezoelectric transducer. A piezoelectric transducer offers a low power reliable device to provide mechanical or vibrational movement.

In some embodiments, the vibrational movement will be adjusted to a frequency that effectively moves dead organisms stored within a storage case in the radiation disinfecting base unit 400. Movement of the dead organisms exposes live organisms that may have otherwise been sheltered from disinfecting radiation.

In still another aspect, in some embodiments, the processor board 403 or other electronic circuitry may control a pattern of light or radiation emitted by the disinfecting radiation source LEDs 401-402. The pattern may include, for example, strobes of a set frequency or variable frequencies.

Some embodiments may also include a display 407. The display 407 will be in logical communication with the processor board 403 and be used to communicate, in human readable form, data relating to the operation of the radiation disinfecting base unit 400.

In another aspect, in some embodiments, one or more UV sensors 410 may monitor an amount of UV radiation present and provide input into a feedback loop that controls an output from disinfecting radiation source LEDs 401-402. Some embodiments include one or more UV sensors 410 that receive UV radiation after the UV radiation has passed through one or more of a lens storage case and a stored lens.

Use of a UV sensor 410 feedback accommodates LEDs that may emit decreasing radiation over the life of the LED and also accommodate different lens storage cases that may differ in transparency characteristics from one case to another.

Figure 5:
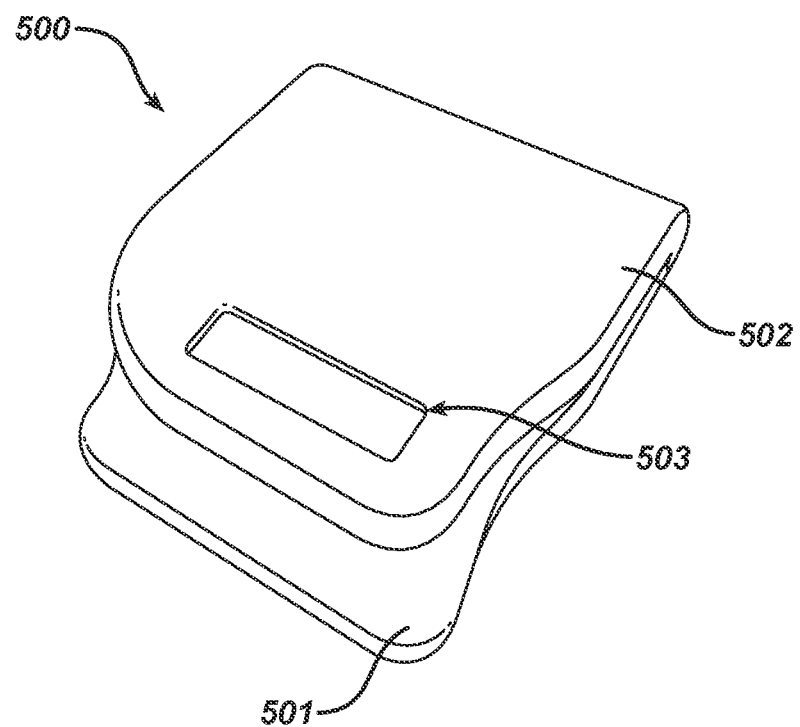
FIG. 5 illustrates a base unit in a closed state with a display.

Referring now to FIG. 5, a radiation disinfecting base unit 500 is illustrated in a closed position. A radiation disinfecting base 501 is covered by a lid 502, in the illustrated embodiments; the lid 502 is hinged to the radiation disinfecting base 501 and folds over on top of the radiation disinfecting base 501. Other embodiments are also within the scope of the invention. As illustrated, a display 503 is located in the lid 502 and may provide an indication of a disinfecting cycle or procedure being executed by the radiation disinfecting base unit 500.

CONCLUSION

The present invention, as described above and as further defined by the claims below, provides apparatus for disinfecting an ophthalmic lens.

The invention claimed is:

1. A base unit for receiving a storage case for storing at least one ophthalmic lens, the base unit comprising:
   a lid;
   a base;
   a receptacle formed within one or both of the lid and the base for receiving the storage case; and
   multiple disinfecting radiation sources mounted to one or both of the lid and the base and configured to emit disinfecting radiation into the storage case, the disinfecting radiation sources are aligned with the storage case via at least one positioning artifact such that the storage case and the ophthalmic lens stored therein are exposed to the emitted disinfecting radiation to disinfect at least a portion of the storage case and the at least one ophthalmic lens stored therein;
   a processor for controlling generation of the disinfecting radiation; and
   a display in the lid for displaying a status of a disinfecting process based upon digital data transmitted by the processor,
   wherein the lid is hinged to the base along one edge and configured to fold over the top of the base and enclose the storage case in the receptacle.

2. The base unit of claim 1, wherein the disinfecting radiation sources emit the disinfecting radiation directly towards the storage case.

3. The base unit of claim 1, wherein the disinfecting radiation sources are an ultraviolet emitting diode configured to emit the disinfecting radiation at a wavelength in the range of about 250 nanometers to 280 nanometers.

4. The base unit of claim 1, additionally comprising a reflective surface for reflecting the disinfecting radiation towards the storage case.

5. The base unit of claim 1, additionally comprising an optic for directing the disinfecting radiation towards one or both of the storage case and the ophthalmic lens stored therein.

6. The base unit of claim 1, additionally comprising a vibration generation device for providing vibrational motion to facilitate disinfection of the ophthalmic lens stored therein.

7. The base unit of claim 1, additionally comprising a power storage device for storing power to operate the base unit.

8. The base unit of claim 1, wherein the processor controls an intensity of the disinfecting radiation emitted from the disinfecting radiation sources based upon a logical control signal generated by the processor.

9. The base unit of claim 1, additionally comprising an audio component operative to provide an audio signal based upon an operation of the at least one disinfecting radiation source.

10. The base unit of claim 1, additionally comprising a digital storage for storing information related to a disinfecting process.

11. The base unit of claim 1, additionally comprising a universal serial bus connector for transferring one or both of data and electrical power to or from the base unit.

12. The base unit of claim 1, additionally comprising a sensor capable of sensing an amount of disinfecting radiation and a feedback loop capable of controlling an output from the disinfecting radiation sources.

13. An ophthalmic lens disinfecting system comprising:
   a base unit having a lid, a base, and a receptacle for receiving an ophthalmic lens storage case, the receptacle being formed within one or both of the lid and the base;
   multiple disinfecting radiation sources mounted to one or both of the lid and the base of said base unit and configured to emit disinfecting radiation into said storage case;
   an ophthalmic lens storage case mountable within the receptacle of the base unit and configured to store at least one ophthalmic lens therein; and
   at least one positioning artifact configured to align the disinfecting radiation sources with the storage case,
   a processor for controlling generation of the disinfecting radiation; and
   a display in the lid for displaying a status of a disinfecting process based upon digital data transmitted by the processor,
   wherein the storage case has a cap and at least one radiation window, and is configured such that upon its insertion into the receptacle it is positioned within a path of radiation emitted by the disinfecting radiation sources such that at least a portion of the storage case and the at least one ophthalmic lens stored therein are exposed to the disinfecting radiation emitted by the disinfecting radiation sources, and
   wherein the lid is hinged to the base along one edge and configured to fold over the top of the base and enclose the storage case in the receptacle.

14. The ophthalmic lens disinfecting system of claim 13, wherein the emitted disinfecting radiation is sufficient to kill an organism on a surface of the storage case.

15. The ophthalmic lens disinfecting system of claim 13, wherein the disinfecting radiation sources emit the disinfecting radiation directly towards the storage case.

16. The ophthalmic lens disinfecting system of claim 13, wherein the storage case comprises an optic for directing the disinfecting radiation toward the ophthalmic lens stored therein.

17. The ophthalmic lens disinfecting system of claim 13, wherein the base unit comprises an optic for directing the disinfecting radiation toward one or both of the storage case and the ophthalmic lens stored therein.

18. The ophthalmic lens disinfecting system of claim 13, wherein the disinfecting radiation sources are ultraviolet emitting diodes configured to emit the disinfecting radiation at a wavelength in the range of about 250 to 280 nanometers.

19. The ophthalmic lens disinfecting system of claim 13, wherein the base unit comprises a reflective surface for reflecting the disinfecting radiation towards the storage case.

20. The ophthalmic lens disinfecting system of claim 13, wherein the storage case comprises a reflective surface for reflecting the disinfecting radiation towards the ophthalmic lens stored within the storage case.

21. The ophthalmic lens disinfecting system of claim 13, wherein the storage case comprises at least one storage compartment configured to store the at least one ophthalmic lens.

22. The ophthalmic lens disinfecting system of claim 21, wherein the at least one storage compartment comprises the radiation window.

23. The ophthalmic lens disinfecting system of claim 21, wherein at least one storage compartment comprises an alignment mechanism configured to position the at least one ophthalmic lens in the storage compartment.

24. The ophthalmic lens disinfecting system of claim 23, wherein the alignment mechanism aligns the ophthalmic lens with the path of the radiation emitted by the disinfecting radiation sources.

25. The ophthalmic lens disinfecting system of claim 13, wherein at least one positioning artifact is an annular depression formed in the cap on the storage case.

26. The ophthalmic lens disinfecting system of claim 13, wherein the processor controls an intensity of the disinfecting radiation emitted from the disinfecting radiation sources.

27. The ophthalmic lens disinfecting system of claim 26, additionally comprising a scanner configured to scan the ophthalmic lens and to log disinfecting information associated with the ophthalmic lens including a time of disinfection.

28. The ophthalmic lens disinfecting system of claim 13, additionally comprising a vibration generation device for providing vibrational motion to facilitate disinfection of the ophthalmic lens.

29. The ophthalmic lens disinfecting system of claim 13, additionally comprising a power storage device for storing power to operate the base unit.

30. The ophthalmic lens disinfecting system of claim 26, additionally comprising a sensor capable of sensing an amount of disinfecting radiation and a feedback loop capable of controlling an output from the disinfecting radiation sources.

31. The ophthalmic lens disinfecting system of claim 13, wherein the disinfecting radiation sources emit the radiation directly towards the radiation window.

32. The ophthalmic lens disinfecting system of claim 13, wherein the disinfecting radiation sources are positioned to emit disinfecting radiation in a direction generally orthogonal to a top surface of the ophthalmic lens storage case.

33. The base unit of claim 1, wherein the multiple disinfecting radiation sources are in an annular arrangement.

34. The ophthalmic lens disinfecting system of claim 13, wherein the multiple disinfecting radiation sources are in an annular arrangement.

* * * * *